(12) United States Patent
Shannon

(10) Patent No.: US 8,070,828 B2
(45) Date of Patent: Dec. 6, 2011

(54) ENHANCED MULTIPLE VISCOSITY LINER

(76) Inventor: Donald T. Shannon, Trabuco Canyon, CA (US)

( * ) Notice: Subject to any disclaimer, the term of this patent is extended or adjusted under 35 U.S.C. 154(b) by 1368 days.

(21) Appl. No.: 11/156,028

(22) Filed: Jun. 17, 2005

(65) Prior Publication Data

US 2006/0111792 A1 May 25, 2006

Related U.S. Application Data

(60) Provisional application No. 60/630,108, filed on Nov. 22, 2004, provisional application No. 60/662,182, filed on Mar. 15, 2005.

(51) Int. Cl.
*A61F 2/78* (2006.01)
(52) U.S. Cl. ........................................... 623/36
(58) Field of Classification Search .............. 623/36, 623/37
See application file for complete search history.

(56) References Cited

U.S. PATENT DOCUMENTS

| | | | |
|---|---|---|---|
| 4,908,037 A | 3/1990 | Ross | |
| 5,728,168 A * | 3/1998 | Laghi et al. | 623/36 |
| 5,746,772 A | 5/1998 | Jacobs | |
| 5,830,237 A | 11/1998 | Kania | |
| 6,136,039 A * | 10/2000 | Kristinsson et al. | 623/36 |
| 6,231,617 B1 | 5/2001 | Fay | |
| 6,454,812 B1 | 9/2002 | Laghi | |

FOREIGN PATENT DOCUMENTS

GB 2 357 725 A * 7/2001
WO WO 03/051241 A1 * 6/2003

* cited by examiner

*Primary Examiner* — David H. Willse
(74) *Attorney, Agent, or Firm* — Snell & Wilmer L.L.P.

(57) ABSTRACT

A novel enhanced liner for prostheses provides for better for either off of the shelf or in customized form, to line a prosthetic used by amputees. Striking a balance between controlling the tear strength and imparting resiliency results in a user friendly product that can be easily donned, and doffed and worn without the drawbacks of the prior art. A unique coating allows the user to remove it like a tubular sock-member, and support comfort and convenience.

8 Claims, 2 Drawing Sheets

ENHANCED MULTIPLE VISCOSITY LINER

RELATED APPLICATIONS

This application claims priority to Provisional Application No. 60/630,108, filed Nov. 22, 2004 and Provisional Application No. 60/662,182, filed Mar. 15, 2005, the contents of each which are expressly incorporated herein in their entirety, as if fully set forth. Full Paris Convention priority is likewise expressly reserved.

BACKGROUND OF THE DISCLOSURE

The present disclosure relates to liners used with prosthetics. In particular, the present disclosure relates to liners which enhance the fit and comfort of prosthetics by having a proper balance between resilience and rigidity.

Longstanding needs in the art are related to the fact that the residual limb of an amputee undergoes structural changes over time, and those who wish to engage in active lifestyles subject their respective prostheses to untoward stresses over time.

Typical amputees' residua tend to decrease in mass over time, owing in part to atrophy, and other stresses to which they are generally subjected. To date, no liners have taken this into account in terms of providing more than one zone of hardness in the liners which will accommodate the needs of active individuals. For this reason the teachings of the present disclosure are offered for consideration and believed to provide an improved way for amputees to lead active lifestyles without any compromise to the fit, comfort or durability of their respective liner systems.

The prior art has turned to adding supplemental structural elements to liners and this impacts the ease of use, comfort and other aspects which users do not enjoy, especially those engaged in active lifestyles. Accordingly, by addressing, ameliorating and overcoming these longstanding issues, the teachings of the instant disclosure are believed to constitute progress in the science and the useful art susceptible of Letter Patent grant, and such relief is hereby earnestly solicited.

SUMMARY OF THE DISCLOSURE

In brief, a novel enhanced liner for prostheses provides for better for either off of the shelf or in customized form, to line a prosthetic used by amputees. Striking a balance between controlling the tear strength and imparting resiliency results in a user friendly product that can be easily donned, and doffed and worn without the drawbacks of the prior art. A unique coating allows the user to remove it like a tubular sock-member, and support comfort and convenience.

According to a feature of the present invention, there is provided a residual limb suspension liner for an amputee having a prosthesis comprising, in combination, a closed-ended, air-tight tubular sleeve adapted to envelop the distal end area of a residual limb, the sleeve formed over its entire length of integral layer construction of different viscosity silicone elastomers, said layers being contiguous and integrally joined to each other along the entire outer surface of the inner layer, and the silicone elastomer of said integral layer construction having two different zones of Shore A durometer hardness aligned with predetermined aspects of the amputees' residuum, and being coated with a lubricious layer, whereby it flexes with axial extension or deformation.

According to another feature of the present disclosure there is provided a residual limb suspension liner for an amputee having a prosthesis comprising, in combination, a closed-ended, air-tight tubular sleeve adapted to envelop the distal end area of a residual limb, said sleeve formed over its entire length of integral layer construction of different viscosity silicone elastomers, said layers being contiguous and integrally joined to each other along the entire outer surface of the inner layer, and the silicone elastomer of said integral layer construction having two different zones of Shore A durometer hardness aligned with predetermined aspects of the amputees' residuum, and being coated with a lubricious layer, whereby it flexes with axial extension or deformation. The silicone elastomer of said integral layer construction can have a lower hardness at a distal end than at a proximal end serving to define it into different zones.

According to yet another feature of the invention, there is provided a prosthetic apparatus, comprising, a prosthetic liner of generally tubular shape having a rounded, closed distal end and an open proximal end for receiving a residuum, a distal attachment plate secured to said prosthetic liner at said distal end thereof, at least an elongate arm extending from said distal attachment plate in a distal-to-proximal direction, said elongate arm being flexible in a radially inward and radially outward direction with respect to a longitudinal axis of said prosthetic liner and said elongate arm being formed of a predetermined material that is substantially nonstretchable in an axial direction, whereby said elongate arm and said distal attachment plate cooperate with one another to spread the weight of a prosthesis attached to said distal attachment plate to thereby reduce a negative pressure in pounds per square inch exerted by said prosthesis during the swing phase of a gait.

BRIEF DESCRIPTION OF THE DRAWINGS

The above-mentioned features and objects of the present disclosure will become more apparent with reference to the following description taken in conjunction with the accompanying drawings in which.

DETAILED DESCRIPTION OF THE DISCLOSURE

The present inventor has discovered that with conventional liners it is extremely challenging to have both the right flexibility and a proper fit. This is because the general approach has been to use reinforced fabric layers, or supplementary stretch prevention mechanisms that interfere with the ability to put liners on, bend them at the knee, and provide the correct balance of comfort and support.

Within the art of cushioned prosthetic liners, the ability to expand radially while maintaining a desired axial dimension is a long unrequited need. It is essential to balance the cushioning effect upon a residual limb's outer surface with the ability to be flexible for doffing and donning.

To address this issue various prior art devices have imparted flexible zones, used singular axial restriction strips, and employed many different types of associated fabric layers. Incorporated by reference herein, as if fully set forth, are U.S. Pat. Nos. 6,136,039 and 6,231,617, both subject to these types of pitfalls.

Top quality, durable and comfortable flexible prosthetic devices have been developed which require improved liners.

(See FIG. 3) Both high-performance prosthetic devices and those designed for moderate activity require comfort and durability, supplied uniquely by the instant technique.

Figure 1:
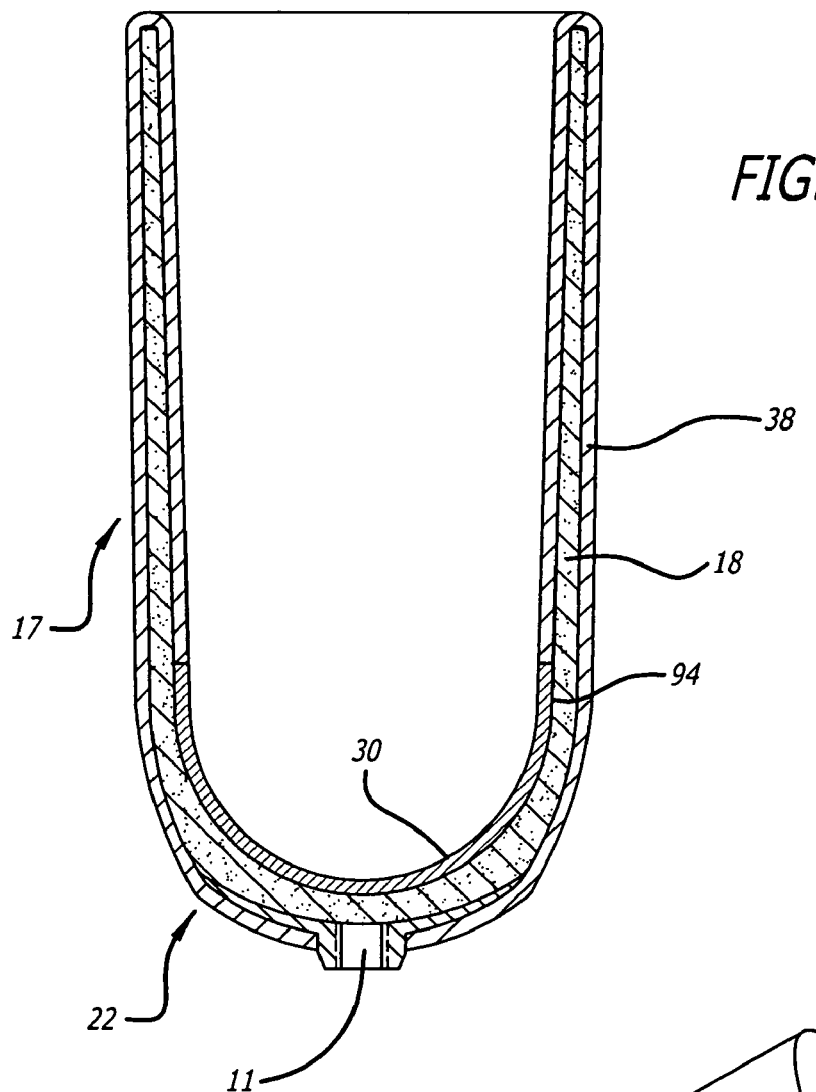
FIG. 1 is a schematic showing an embodiment according to the teachings of the present disclosure.

Referring now to FIG. 1, liner 22 is shown generally. According to the instant teachings an outer layer, functioning effectively as low friction sheath 38, works by coating for facilitating donning and wearing of a prosthesis on a residual limb. The outer layer/coating/sheath 38 is configured to remain between the residual limb and the prosthesis during normal use of the prosthesis.

According to an embodiment of the instant disclosure, zone 30 is softer, or is one having a Shore A durometer hardness of 30, which is aligned with predetermined aspects of the amputees' residuum, and being coated with lubricious layer 38, whereby it flexes with axial extension or deformation, whereas second zone 17 for example extending toward the upper end of the prosthetic liner may have a Shore A durometer of 50. The lubricous layer 38 can be sprayed, wiped, vapor deposited or otherwise applied.

Several different ways are used to accomplish this including treatment of zone 30 with other treating or coating elements 94 during processing. Principal elastomer 18 is coated entirely by coating layer 38, which may be the Parylene brand of product discussed below.

A novel system for facilitating the donning and wearing of a prosthesis on a residual limb by reducing the frictional forces between the residual limb and the prosthesis, is taught by the instant disclosure.

Thousands of people undergo amputations. The predominant causes of amputation are peripheral vascular disease and diabetes. Additional causes of amputation include trauma, congenital abnormalities, and diseases such as cancer. In many cases amputees are elderly, have poor physical strength, and/or have fragile skin conditions. Thus, physical limitations may inhibit the ability of an amputee to adequately don a prosthesis. Additionally, shear or other forces within the socket of the prosthesis may lead to sores developing on fragile skin. The present disclosure addresses each of these concerns.

High frictional and compressional forces between the residual limb of an amputee and the prosthesis may pose many other problems and concerns. Friction within a prosthetic socket interface often increases proximal bunching of prosthetic socks, adductor rolls, proximally directed pressure of soft tissue.

If these issues are not addressed adequately, the amputee's functional abilities are often limited due to discomfort, fitting limitations, and/or the risk of developing sores on the residual limb. These risks are of great concern for amputees, especially those with conditions that may cause delayed healing, such as PVD or diabetes.

With some traumatic or congenital related amputations, the residual limb itself may present unique fitting considerations due to tissue consistency or irregular bone structure of the residual limb. Thus, the structure of the residual limb itself may cause difficulty in optimally fitting a prosthesis for ease of donning, comfort, and function.

The composite elastic material of the instant disclosure may be molded to provide a thicker anterior wall and a thinner posterior wall with a smooth transition between the anterior and posterior walls, depending on the particular usage required, and those skilled in the art understand that the exemplary descriptions herein are meant to cover either type of version.

Referring back to FIG. 1, the composite elastic material is covered with a specialized coating layer 38, which may be used as a sealing sleeve between a prosthetic device and a residual limb. The composite elastic material may contain one or more skin treating agents blended into the silicone.

It is highly desirable to provide a relatively soft cushion in contact with or adjacent to the skin of the user of a prosthetic device for comfort. However, the cushion must be relatively inert with respect to the skin of the user, be readily washable and feel comfortable, all achieved with the instant disclosure.

As the thickness of the silicone elastomer cushion grows, so does the weight of the suction liner. It is highly desirable to obtain the soft cushioning effect of a silicone elastomer in a suction liner application while reducing the overall weight of the liner attributable to the silicone elastomer.

It is desirable to form a relatively thin posterior wall and a relatively thick anterior wall to provide cushioning on the anterior wall while avoiding interference with movement of the prosthetic user, particularly with a below-the-knee amputee.

The composite elastic material also includes a coating layer 38 intimately bonded to both sides of the silicone layer described above. Depending on the application, this can be revised, adjusted, changed or customized.

The composite elastic material may be used in the form of a tubular prosthetic suction liner having a closed distal end and dimensioned and configured so as to be rollable onto a distal end of a residual limb of a prosthetic device user, with a silicone elastomer layer on the interior of the liner and an elasticized zone on the exterior of the liner. Such residual limb receiving liners are used between a socket of a prosthetic appliance and the residual limb of the appliance user.

The composite elastic material also may be used as a sealing sleeve that is tubular in form and open at opposed ends, with the silicone elastomer layer covering the inside wall of the sleeve and the elasticized zone covering a portion of the exterior of the sleeve. Such a sleeve is dimensioned and configured to be installed as a suction seal between a prosthetic device and the residual limb of the prosthetic device user, with the silicone elastomer layer facing towards the location of the residual limb with the upper end of the prosthetic device located within the sleeve.

A rigid prosthetic connector element may extend through aperture 11 such that the prosthetic may be attached to the distal end of the suction liner by embedding the connector element in a cured silicone elastomer distal end cap adhered to the distal end of the suction liner. The connector is sufficiently exposed while embedded in the end cap so as to provide access to a prosthetic connector pin that may be fastened to the connector. The silicone elastomer distal end cap may be formed of a silicone elastomer having a higher durometer than the composite elastic silicone elastomer layer to provide a more rigid support zone at the distal end of the suction liner.

As is known, the suction liner may be tapered conically inwardly towards its distal end from its open proximal end, and wherein the sleeve has a circular outer wall having radii of curvature centered along a first longitudinal sleeve axis of external symmetry extending longitudinally centrally within the sleeve, a circular curved inside anterior wall portion extending along a sleeve length and having first radii of curvature centered on a second longitudinal axis of anterior curvature extending longitudinally along said sleeve length and a circular curved inside posterior wall portion having second radii of curvature centered on a third longitudinal axis of posterior curvature extending along said sleeve length; said first, second and third longitudinal axes lying in a common longitudinally and transversely extending plane bisecting the anterior and posterior wall portions, and wherein said second and third axes are spaced apart at predetermined offset distance on opposed sides of said first axis to thereby define an anterior wall portion that is thicker along the sleeve length than the posterior portion; and further wherein the anterior and posterior wall portions intersect each other along said sleeve length on the sleeve interior along diametrically opposed inner transition wall portions that extend tangentially relative to the adjoining anterior and posterior wall portions along said sleeve length, whereby the interior wall of the suction sleeve along the transition wall portions is free of rapid changes in thickness, curvature or cross-section profile.

A spherical curved inside distal wall portion may be provided within the suction liner, with said distal wall portion joining the adjoining interior wall of the suction liner along a tangency. This forms a smooth transition between the inside distal wall portion and the adjoining interior wall of the suction liner that may likewise be featured. The thickness of the adjacent interior wall of the suction liner may be the same as the thickness of the anterior wall of the suction liner.

When provided with an optional layer bonded on one side of the silicone elastomer layer, a thin continuous coating of second cured elastomer material is provided on the elasticized zone between the fabric and the principal silicone elastomer layer. The thin coating of the second elastomer material partially penetrates and is embedded in the principal layer and forms a continuous coating over the principal silicone elastomer layer. The silicone elastomer coating material is fully stretchable elastically at least to the same extent as the principal silicone layer to which it is attached and adhered.

The thin coating layer of silicone elastomer provides a good bonding surface for any supplemental composite elastic layer that may need to be attached.

Preferably, the silicone layer is obtainable under Product No. CF15-2188 from NuSil Technology of Carpinteria, Calif. Physical properties of the combined composite elastic layer 18, coating 38 and elasticized zones incorporated thereon include a tensile strength greater than 1 Pa, preferably greater than 2 Pa; and a 100% modulus of 5 to 300 kPa, preferably 55 kPa.

The aperture 11, may receive a distal end cap, which may be formed of a silicone elastomer including 98% by weight silicone rubber, type MED-4950 or type MED-4050 or type CF15-2188, all available from NuSil Technology, with the balance (2%) constituted of a color mixture, for example a color powder blended from 12.5 parts Lucas color No. 2408, 12.5 parts Lucas color No. 2439 and 75 parts Lucas color No. 2510 all obtainable from Fr. Schoenfeld GmbH and Co. Further properties of MED-4950 as published by NuSil Technology include: the material uses a platinum cure system; a press cure time of 50 minutes at 150.degree. C.; durometer 45-55; tensile strength 1000 psi (6.9 MPa); elongation 400%; and a tear strength 230 ppi (40.3 kN/M).

Referring still to FIG. 1, coating layer 38 may be Parylene (available from Para Tech Coating, Inc., Aliso Viejo, Calif., 92656) which is a vacuum deposited film originating from a powder (di-para-xylylene). The powder is converted to a gaseous monomer that condenses and polymerizes on substrates at room temperature. Unlike dip or spray coatings, condensation coating does not run off or sag, is pinhole free, will not bridge, so that holes can be coated evenly, coat over edges, and internal areas. Masking can be used if desired on areas not to be coated. See U.S. Pat. Nos. 4,945,856; 5,167,718; 5,263,033; and 5,078,091 each of which is expressly incorporated herein by reference, as if fully set forth herein.

The Parylene process is a relatively simple vacuum application system, which starts with a dimer. The dimer is placed in a vacuum system and converted to a reactive vapor. When passed over room temperature objects, this vapor will rapidly coat them with a polymer. The end result is an almost impervious uniform coating.

Parylene is not produced or sold as a polymer. It is not practical to melt, extrude, mold or calendar as with thermoplastics. Nor can it be applied from solvent systems. Actually, many of the advantages found in Parylene coatings, unlike epoxies, urethanes or silicones are a direct result of the coating deposition process.

Parylene is extremely resistant to chemical attack, exceptionally low in trace metal contamination, with superior dielectric strength, low dissipation factor, and other superior electrical properties that remain virtually constant with changes in temperature (please refer to Gaixyl® specification sheet available at www.parylene.com). In current commercial applications, Parylene is deposited in thickness ranging from a few thousand angstroms to about 50 microns depending on the function the Parylene film has to perform. This provides physical barrier properties equal to or better than, the 2-6 mil thickness of epoxies, silicones, urethanes or other conventional coatings, which generally require multiple applications for accurate protection. The small static and dynamic friction coefficients allow Parylene to serve as a "dry film" lubricant. There are no environmental concerns by using Parylene since no catalysts or solvents are required.

Parylene C is poly-monochoro-para-xylylene, and is the most widely used member of this unique polymer series due to its excellent barrier properties. It offers significantly lower permeability to moisture and gases, such as nitrogen, oxygen, carbon dioxide, hydrogen sulfide, sulfur dioxide and chlorine, while retaining excellent electrical properties.

One of the most critical and important aspects of vapor deposition is the handling and preparation of parts for coating.

Another silicone suspension liner according to the instant disclosure for a prosthesis includes a soft inner silicone elastomer layer and a relatively harder outer silicone elastomer layer, with both layers being formulated to provide desired physical characteristics of the liner. An elasticity material and a prosthesis connecting element may be provided in the distal end area of the liner. The softer inner layer closely conforms to the residual limb that is to be fitted to a prosthesis while the harder outer layer provides durability and strength for the liner.

Figure 2:
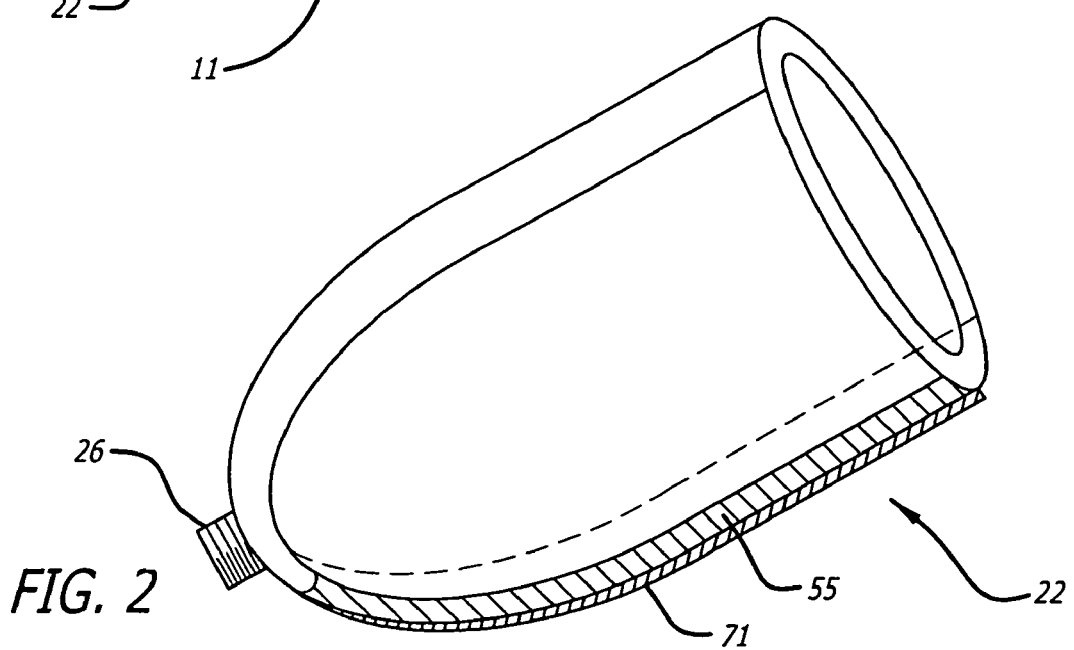
FIG. 2 shows a partial plan view of an embodiment of the present disclosure.

Referring now to FIG. 2, a silicone elastomer liner 22 is air-tight when donned over a residual stump. Longitudinal reinforcement arm 71 permits users to attach liner 22 between their residuary limb and threaded socket 26 optimally is included to receive a prosthesis locking pin (not shown). Likewise, a supplemental zone 55 may be included for users requiring further strength or stiffness in liner 22.

The entire liner 22 is formed of desired layers of silicone elastomer to be described in more detail below, the interface between the layers constituting a seamless, integral, permanent connection between the layers.

A relatively rigid prosthesis connecting "umbrella" element (not shown) having a concave curved configuration as shown and/or a threaded socket 26 for receiving a prosthesis locking pin is provided at the distal end 12 of the liner 22, preferably embedded in the silicone elastomer. A connecting element (not shown) may alternatively intimately bond to the silicone elastomer constituting the liner 10.

Figure 3:
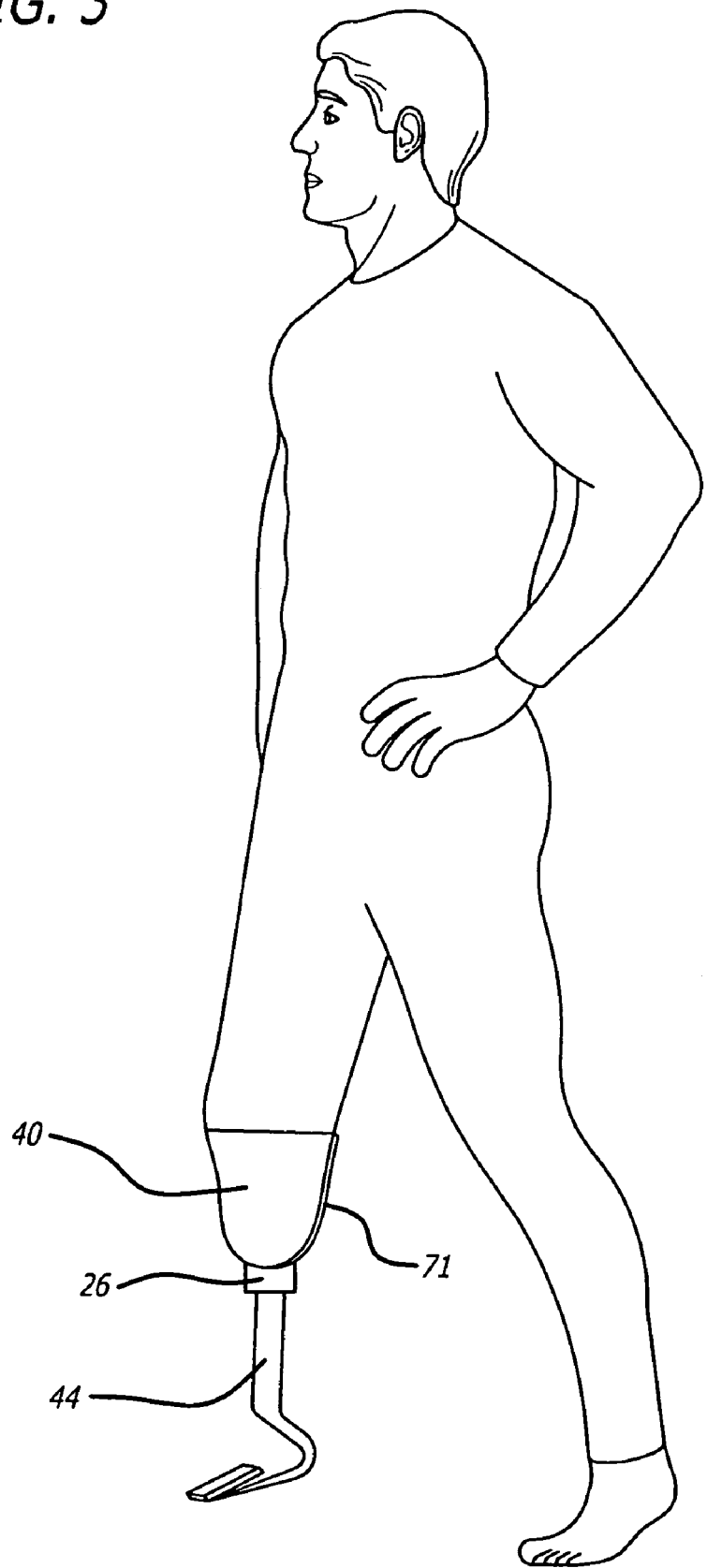
FIG. 3 is another schematic view showing an amputee using, an exemplary embodiment of the present disclosure.

Referring now to FIG. 3, a typical active user, for example, a triathlete is shown for whom the features of the present disclosure are important. Liner 40 may include optional longitudinal extension arm 71 and prosthesis pin (not shown) passes through socket 26 (threaded or otherwise) to anchor prosthetic 44.

Prosthetic 44 is for example, the RENEGADE® brand of prosthetic available from Freedom Innovations and Freedom Science and Technology, Irvine, Calif. Likewise, prosthetic 44, may be one equipped with a sensor or microprocessor embedded therein.

The liner 22 is fabricated in a sufficient number of sizes to accommodate various sizes of residual limbs. In use, a liner of the type described is rolled up from the proximal to the distal end, placed over the distal end of the residual stump and rolled back up or "donned" over the stump like a stocking.

Fabricating the sleeve liner is carried out as known to those skilled in the art or as follows. For each specific liner size, three mold sections consisting of two outer mold sections and an inner mold section are provided. The first shot outer mold section is configured to give a specific thickness of the liner inner layer 18 while the second shot outer mold section is configured to provide a specific thickness of the outer layer covering the inner layer 18, the matrix and the connecting element. The inner mold section is a male form conforming to the inner surface of the liner. The outer mold sections are female molds that fit over the inner mold and provide a space between the inner and outer mold sections for receiving liquid silicone elastomer that is injected under pressure between the mold sections during the liner mold or casting process.

To form the layer slightly above ambient or room temperature (typically 35° C.) the first shot outer mold is placed over the inner mold, centered and secured. Silicone material forming the inner layer is injected into the top of the outer mold section under a pressure of 40-100 psi and the mold is filled. The temperature is elevated to a desired level (70-125° C.) for curing or vulcanizing the first layer and then lowered after the silicone material has set.

The connecting element is intimately bonded between the two layers as well so that the entire structure of the liner is integrally connected together.

The molded liner is then removed from the inner mold section and prepared for packing and shipment.

The silicone elastomer used to form the inner layer 18 comprises a vinyl terminated polydimethylsiloxane (vinyldimethylsiloxy terminated dimethylpolysiloxane) cured or vulcanized by reaction with a suitable crosslinker. The silicone elastomer is reinforced with silica (preferably fumed silica having a surface area of 200 m.sup.2/g.) and this increases the strength of the cured or crosslinked silicone. The degree of crosslinking can be adjusted to some extent by adjusting the concentration of crosslinker. The component in the elastomer that the crosslinker reacts with is typically a vinyl group that is on the ends of the polysiloxane. The end groups on the polysiloxane also control the viscosity of the silicone and the concentration can be varied to allow a formulator to manufacture polysiloxanes of various viscosities. Specifically, more than one end blocking moiety is used to provide control of viscosity and level of crosslinking somewhat independently of each other. The preferred viscosity is in the range of 90,000-100,000 cPs. Non-functional endblocking (trimethyl siloxy) is used in conjunction with vinyl endblocking (vinyldimethyl siloxy) to allow the production of a polysiloxane with a lower vinyl concentration than would otherwise be necessary if vinyl endblocking was used exclusively. This technique permits the production of low viscosity silicones having a somewhat lower density crosslinking than is commonly used in silicone elastomers.

For example, alternate versions may include compositions containing trimethyl silyl treated silica as a reinforcer in the weight ratio of approximately 12 to 45 parts of reinforcer to 100 parts of polymer. The preferred invention contains 17 parts of silica to 100 parts of polymer. The silica must be treated with a reagent to neutralize the active sites on its surface, usually using hexamethyldisilazane.

The elastomer is made in two components, called part "A" and "B". Part A is constituted of the polydimethylsiloxane that is vinyl and methyl terminated. A platinum catalyst is used, the catalyst comprising a complex of platinum with vinyl-containing oligosiloxanes (complex of platinum and divinyltetramethyldisiloxane with typical levels of active platinum of 5 to 50 parts per million.

Part B of the two components of the elastomer includes a polydimethylsiloxane and silica identical to that in part A. This part B also includes a polydimethylsiloxane with hydrogen on the chain commonly called methyl hydrogen which acts as a crosslinker. With the sum of the mass of polydimethylsiloxane and silica constituting 100 parts, crosslinker concentration can vary from as low as 0.3 to as high as 4 parts per hundred parts. A crosslinking inhibitor is included in part B that comprises an oligosiloxane with high concentration of vinyl-containing substituents of any of the class of compounds known as acetylinic alcohols. The preferred inhibitor is tetravinyl tetramethyl cyclotetrasiloxane. The inhibitor may be used in concentrations as low as 0.02 parts per hundred parts to as high as 0.5 parts per hundred parts.

In forming the inner layer, parts A and B are mixed together before injection in the mold in a 1:1 ratio by weight.

The silicone elastomer just described above is obtainable from NuSil Technology of Carpinteria, Calif., under product designation CF13-2188.

This silicone material is also obtainable from NuSil Technology of Carpinteria, Calif., under product designation CF3-2188-1. The silicone elastomer is addition-cured using a platinum catalyst of the type described above in connection with the NuSil product CF13-2188 silicone elastomer. The silicone elastomer used in the outer layer also is provided as two components, parts "A" and "B".

Part A is made from polydimethylsiloxane that is vinyl terminated and a second polydimethylsiloxane that is trimethyl terminated. Trimethyl terminated polymer is included at a concentration of 1-10% and silica is included in the formulation for reinforcement. The viscosity of the uncured part A elastomer used to form the outer layer of the liner is 250,000-800,000 cPs. The silica is treated with a reagent to neutralize the active sites on its surface using, preferably, hexamethyidisilazane, with the concentration of silica being in the range of 1245 parts per hundred parts of polysiloxane, with a preferred concentration being 25 parts per hundred per one hundred parts of polysiloxane. Titanium dioxide is added to the part A component of the silicone elastomer in concentration sufficient to color it opaque white in a concentration of 2-15%, if a white color is desired. A platinum catalyst is added to the part A component, the catalyst comprising a complex of platinum and divinyltetramethyldisiloxane with a level of active platinum typically from 5-50 parts per million.

The part B component of the CF3-2188 silicone elastomer comprises polydimethylsiloxane and silica identical to that used in part A described above and a crosslinker. Typically, part B contains no pigment, and is translucent. Assuming the sum of the mass of polydimethylsiloxane and silica to constitute 100 parts, polydimethylsiloxane with hydrogen on the chain (commonly called methyl hydrogen) is used as the crosslinker in concentrations extending from 0.3 to 4.0 parts per hundred. A crosslinking inhibitor is added to part B in the form of an oligosiloxane with a high concentration of vinyl-containing substituents or any of the class of compounds known as acetylinic alcohols to control rate of crosslinking. The preferred inhibitor is tetravinyl tetramethyl cyclotetrasiloxane in concentrations from about 0.02 parts per hundred to 0.5 parts per hundred.

When forming the elasticized layer 18, parts A and B of the NuSil CF3-2188-1 silicone elastomer are mixed in a ratio of 1:1 to cause crosslinking by hydrosilylation, with the inhibitor allowing control of the rate of crosslinking of the two parts when they are mixed together.

It will be seen from the Shore hardness properties of the inner layers 18, 38 that the inner layer is considerably softer than the outer layer, and has a lower tear strength than the outer layer. The outer layer possesses greater hardness and tear strength, which serves to reinforce the softer inner layer and provides a product that is both strong and durable, while very comfortable for the user. The ability of the inner layer 18 to conform to the skin surface of the residual limb of the user reduces any gaps between the skin and the inner layer which tends to reduce perspiration between the residual limb and the inner surface of the liner, a characteristic that is highly desirable in a liner of this type.

Friction properties of the inner, softer liner against the skin of the residual limb are such that a higher shear force is needed to cause slippage between the inner layer and the skin as compared with prior art silicone elastomer liners, which enhances the suspension properties and comfort of the liner.

The viscosity of the liquid silicone elastomer used to form both the inner layer 18 and the outer layer is low enough to allow rapid injection molding of large parts. The preferred viscosities are in the range of 90,000 to 100,000 cPs. The formulation of the outer layer may be varied, provided that the physical property characteristics of the outer layer as described above remain essentially consistent, particularly with regard to a Shore OO hardness which must be higher than that of the inner layer 18. Typically, the tensile and tear strengths of the outer layer will be higher than these strengths of the inner layer. It is also preferred that the outer layer have a higher elongation and modulus than the inner layer.

Coloration of the liner is optional, and one example has been described above wherein the inner layer is colored white and the outer layer is translucent.

The longitudinal edges of strips 40 may be interpreted as depicting seam lines created by sewing a nonstretchable thread along the extent of the prosthetic liner.

Thus, when embedded in a prosthetic liner formed of silicone or other suitable cushioning material, or positioned on the surface thereof, the inherent bias of the prosthetic liner allows it to conform to the residual limb as it expands and contracts, without substantial resistance offered by said fingers, arms, strips, or seams.

Since the fingers, arms, epoxy strips, nonstretchable material strips are not extensible or contractible in an axial direction. Thus, they prevent milking of the residuum while allowing it to radially expand and contract.

Significantly, the novel arms, strips or seams create a structure that has the effect of substantially increasing the inner surface area of the prosthetic liner over which a prosthesis is suspended. Substantially the entire inner surface area of the prosthetic liner is harnessed. In a commercial embodiment of the novel cushioned prosthetic liner, the weight of a ten pound prosthesis is spread out over a one hundred sixty eight square inch area. Thus, when the prosthesis is suspended during the swing phase of the gait, the negative pressure is only six hundredths of a pound per square inch (0.06 lbs/in.sup.2). This represents a revolutionary improvement over the negative five pounds per square inch stresses that appear in earlier prosthetic liners.

Since the elongate arms, strips, or seams do not completely surround the prosthetic liner, they do not inhibit flexing of the prosthetic liner in the anterior region and thus the knee of a wearer is freely bendable.

This invention represents a major breakthrough in the art of prosthetic liners. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A residual limb suspension liner for an amputee having a prosthesis comprising, in combination:
   a closed-ended, air-tight tubular sleeve adapted to envelop the distal end area of a residual limb;
   said sleeve formed over its entire length of a principal elastomer coated entirely by a coating layer on an inner surface of the principal elastomer and an outer surface of the principal elastomer, said principal elastomer and said coating layer being of different viscosity silicone and being contiguous and integrally joined to each other;
   said coating layer on the inner surface of the principal elastomer having two different zones of hardness aligned with predetermined aspects of the amputee's residuum, and being formed at least partially from a lubricious layer, whereby it flexes with axial extension or deformation.

2. The residual limb suspension liner of claim 1, wherein the different zones of hardness comprise a first zone having a Shore A durometer hardness of about 30 at a proximal end and a second zone having a Shore OO durometer hardness of about 50 at a distal end.

3. The residual limb suspension liner of claim 2, the lubricious layer further comprising at least one of a vapor deposited, sprayed, filmed, painted, coated and melted layer.

4. The residual limb suspension liner of claim 3, wherein said coating layer includes a vacuum deposited film originating from di-para-xylylene.

5. A residual limb suspension liner for a prosthesis which comprises, in combination:
   a closed-ended, air-tight tubular sleeve adapted to envelop a distal end area of a residual limb;
   said sleeve formed over its entire length as a bilayer construction of an inner layer and an outer layer of different silicone elastomers, said inner layer and said outer layer being contiguous and integrally joined to each other along an outer surface of the inner layer;

the inner layer of said bilayer construction having a lower hardness at a distal end than at a proximal end serving to define it into different zones; and an elasticity controlling construction extending from the distal end in a peripheral section, the construction causing a distal end area to be substantially inelastic in the axial direction without interfering with radial elasticity of the silicone elastomers within a range of distension of the liner during normal use.

6. The residual limb suspension liner of claim 5, wherein the different zones of hardness comprise a first zone having a Shore A durometer hardness of about 30 at the distal end and a second zone having a Shore A durometer hardness of about 50 at the proximal end.

7. The residual limb suspension liner of claim 6 wherein the inner layer is formed at least partially from a lubricious layer comprising at least one of a vapor deposited, sprayed, filmed, painted, coated and melted layer.

8. The residual limb suspension liner of claim 7, wherein said bilayer construction includes a vacuum deposited film originating from di-para-xylylene.

* * * * *